United States Patent
Williams, III et al.

(10) Patent No.: US 8,333,805 B2
(45) Date of Patent: Dec. 18, 2012

(54) COMPOSITE JOINT IMPLANT

(75) Inventors: Philip F. Williams, III, Teaneck, NJ (US); Christopher DeMaria, Glen Rock, NJ (US); Edward J. Laganis, Edgewater, NJ (US); Anthony J. La Rosa, Wharton, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 974 days.

(21) Appl. No.: 11/384,921

(22) Filed: Mar. 20, 2006

(65) Prior Publication Data
US 2007/0233266 A1    Oct. 4, 2007

(51) Int. Cl.
*A61F 2/38* (2006.01)
(52) U.S. Cl. .................................... 623/20.35
(58) Field of Classification Search .............. 623/20.14, 623/20.15, 20.19, 20.28, 20.31, 20.35, 20.36
See application file for complete search history.

(56) References Cited

U.S. PATENT DOCUMENTS

| | | | |
|---|---|---|---|
| 3,708,805 A * | 1/1973 | Scales et al. | 623/20.12 |
| 4,268,920 A * | 5/1981 | Engelbrecht et al. | 623/20.26 |
| 5,171,282 A * | 12/1992 | Pequignot | 623/20.35 |
| 5,258,032 A | 11/1993 | Bertin | |
| 5,358,529 A | 10/1994 | Davidson | |
| 5,443,513 A | 8/1995 | Moumene et al. | |
| 5,464,406 A | 11/1995 | Ritter et al. | |
| 5,549,684 A * | 8/1996 | Amino et al. | 623/20.35 |
| 5,609,642 A | 3/1997 | Johnson et al. | |
| 5,683,470 A | 11/1997 | Johnson et al. | |
| 5,702,460 A | 12/1997 | Carls et al. | |
| 5,776,201 A | 7/1998 | Colleran et al. | |
| 5,879,393 A | 3/1999 | Whiteside et al. | |
| 6,074,424 A * | 6/2000 | Perrone et al. | 623/20.3 |
| 6,132,468 A | 10/2000 | Mansmann | |
| 6,827,739 B2 | 12/2004 | Griner et al. | |
| 6,916,324 B2 | 7/2005 | Sanford et al. | |
| 2001/0016778 A1 * | 8/2001 | Badorf et al. | 623/20.35 |
| 2002/0198528 A1 | 12/2002 | Engh et al. | |
| 2003/0158606 A1 * | 8/2003 | Coon et al. | 623/20.15 |
| 2004/0054417 A1 | 3/2004 | Soffiati et al. | |
| 2004/0153086 A1 | 8/2004 | Sanford | |

(Continued)

FOREIGN PATENT DOCUMENTS

DE    923 383    2/1955

(Continued)

OTHER PUBLICATIONS

T. M. Wright et al; Failure of Carbon Fiber-Reinforced Polyethylene Total Knee-Replacement Components; The Journal of Bone and Joint Surgery, vol. 70-A, No. 6, pp. 926-932, Jul. 1988.

*Primary Examiner* — Bruce E Snow
*Assistant Examiner* — Melissa Hoban
(74) *Attorney, Agent, or Firm* — Lerner, David, Littenberg, Krumholz & Mentlik, LLP

(57) ABSTRACT

The present invention relates to a femoral component for use in connection with knee anthroplasty. The implant includes a support having a contoured inner bone engaging surface, and a shell affixed to the support. The shell has an outer surface spaced so as to provide an articulation surface for engaging the tibia that substantially replicates the shape of a femoral condyle, and an inner surface for receiving an outer surface of the support. The support bone engaging surface is structured to mate with a prepared surface of the distal femur and the support spaces the shell outer surface at a predetermined distance from the prepared surface.

18 Claims, 4 Drawing Sheets

U.S. PATENT DOCUMENTS

| | | | |
|---|---|---|---|
| 2004/0236429 A1* | 11/2004 | Ensign et al. | 623/20.32 |
| 2005/0043804 A1* | 2/2005 | Gordon et al. | 623/17.16 |
| 2005/0203629 A1 | 9/2005 | Cipolletti et al. | |
| 2005/0203630 A1* | 9/2005 | Pope et al. | 623/20.21 |
| 2008/0004709 A1* | 1/2008 | O'Neill et al. | 623/20.35 |
| 2009/0125115 A1* | 5/2009 | Popoola et al. | 623/20.14 |

FOREIGN PATENT DOCUMENTS

| | | |
|---|---|---|
| EP | 0 378 928 | 7/1990 |
| EP | 0 768 066 | 4/1997 |
| EP | 1 384 455 | 1/2004 |
| FR | 2 851 156 | 8/2004 |

* cited by examiner

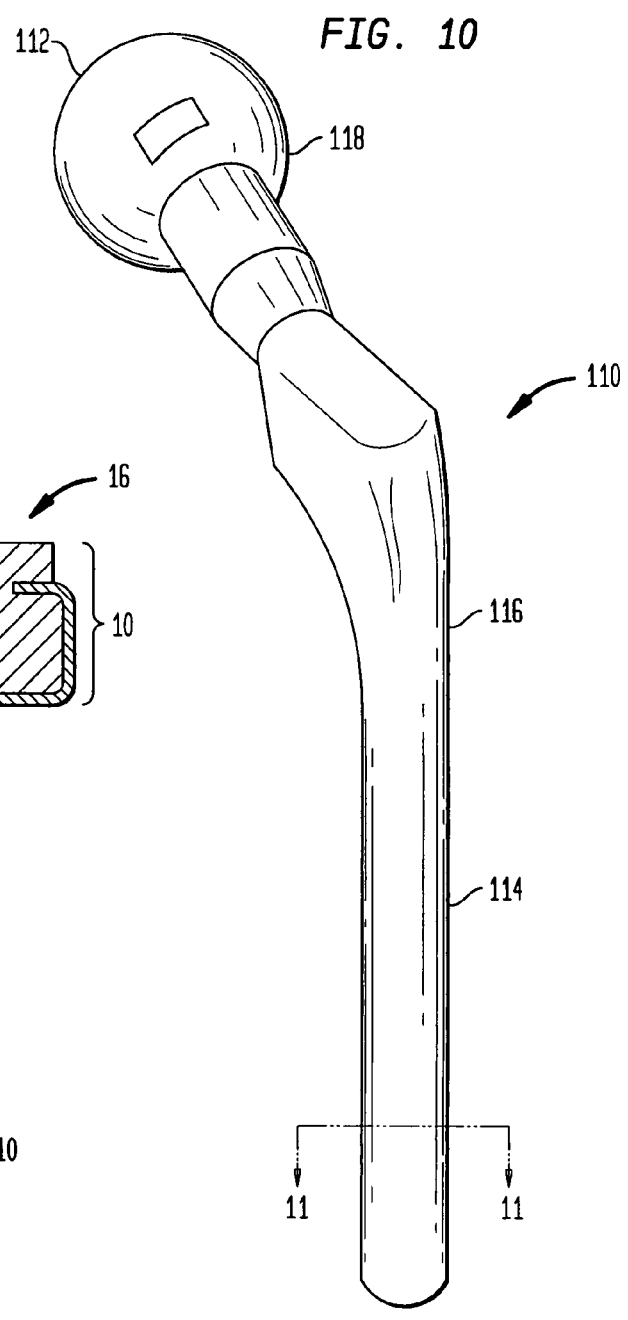

COMPOSITE JOINT IMPLANT

BACKGROUND OF THE INVENTION

Total knee replacement ("TKR") is a commonly-used procedure for correcting deformities and repairing damage to the knee joint. The procedure used for TKR is generally known in the art and includes many variations. Generally, such a procedure includes exposing the knee joint by forming at least one incision through the soft tissue in the knee area and retracting the wound. The joint is then resected, which includes removing the damaged portions of the joint. This typically includes removing one or both of the femoral condyles and/or the tibial plateau, which is typically accomplished by forming a series of cuts according to any one of various patterns. The cuts are typically made so that the bone can accept an artificial replacement for the resected portions of the joint. As the precise anatomy of the knee on which TKR is preformed varies significantly among patients, it is necessary to provide artificial replacements for the knee components in various shapes and sizes. It is also necessary to form the cuts in the bones of the knee joint to appropriately accept the implant that best suites the anatomy of the individual joint as best suited for the patient.

In order to facilitate the appropriate joint resection and artificial joint selection, various trial implants have been developed are used in "trial reduction" of the resected joint. To assist in trial reductions, a number of differently sized "trial" joint implants (which are also referred to as "provisional" implants) are supplied. After a preliminary estimate of the appropriately sized implant is made, trial implants are inserted into the resected joint, usually on both the femur and on the tibia. The implant is then examined for proper fit, and the joint is tested for proper kinematics. If the fit of the trial is improper, different trials are selected in succession until proper fit is achieved. Selection of differently sized trials may require further joint resection. Once a proper size determination has been made, a permanent joint implant of a size which corresponds to that of the appropriately-sized trial is affixed within the joint. In TKR this typically includes affixing permanent implants into both the femoral and the tibial components of the knee. A similar trial reduction procedure is used to determine proper implant fit in a total hip replacement (THR) procedure.

Trial femoral components must accurately match the geometry of the permanent implant to be used in TKR. Further, femoral trials must be sufficiently rigid to replicate proper joint kinematics. Costs associated with manufacturing such trial components has lead to known trial components being made so as to be reusable throughout multiple procedures. Reuse of trials requires that the trials be sterilized prior to each use, which is typically done using an autoclave procedure. Such a procedure is somewhat rigorous with respect to the items subjected thereto, which further requires robust construction of the trials. In response to these requirements, known trial components have been manufactured from cast cobalt-chromium (CoCr) or stainless steel ("SS"), both of which can withstand multiple autoclave cycles and are sufficiently rigid to provide accurate trial reduction. However, the processing required to impart the necessary geometry onto these materials requires many secondary operations, such as CNC grinding or polishing. The material properties of CoCr and of SS are such that these secondary operations require relatively low feed and tool speed rates to properly create the complex geometries that are part of the trial. Each of these secondary operations is, thus, costly and time consuming, leading to a large overall cost increase of trial components.

In addition to the cost associated with processing the cast materials of typical trials, the density of the material can be quite high, resulting in a relatively heavy component. Each trial component may weigh approximately 1-1.5 pounds, a weight which becomes problematic due to the methods employed during TKR and THR procedures. Currently, validated sterilization methods require each component that may potentially enter the sterile field to be steam-sterilized prior to surgery (typically via an autoclave process) As a result, all surgical tools that may potentially be used during TKR and THR procedures are kitted and held in sterilization trays. The kitting of instruments is based on the surgical steps for which they are required as part of a particular procedure. As a result, all instruments required to complete a step are preferably stored in one tray or case. Multiple trays are then placed into a sterilization case and the case is processed through the sterilization process and brought into the operating room. In the case of femoral trials, because final determination of femoral size is made interoperatively, all such devices for a given TKR system are housed on a single tray and brought into the operating room together. A typical TKR system can have eight differently sized trials for both the left and right femoral components, resulting in sixteen femoral trials being stored in a single sterilization tray. Based on the average trial weight, the fully-loaded tray may twenty pounds or more. When combined with the other trays contained in the sterilization case, total case weight is significant. The same problem applies for THR procedures: as with femoral sizing, proximal stem sizing must be performed interoperatively. Therefore, a fully-loaded THR tray may also weigh upwards of twenty pounds.

It is therefore desired to provide a trial component that has a reduced weight, and which reduces costly process steps, while retaining the desired characteristics for such a component.

As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

SUMMARY OF THE INVENTION

The present invention relates to a femoral component for use in connection with knee anthroplasty. The implant includes a support having a contoured inner bone engaging surface, and a shell affixed to the support. The shell has an outer surface spaced so as to provide an articulation surface for engaging the tibia that substantially replicates the shape of a femoral condyle, and an inner surface for receiving an outer surface of the support. The support bone engaging surface is structured to mate with a prepared surface of the distal femur and the support spaces the shell outer surface at a predetermined distance from the prepared surface.

The femoral component of the present invention may have a support that is formed from a plastic. Further, the femoral component may have a shell that is made from a metal, such as stainless steel or cobalt chrome, which may be formed using a hydroform process. Preferably, the shell is further shaped so as to provide an outer profile having a rib extending therefrom in a direction substantially away from the articulation surface. Further preferably, the support is made from a polymeric material and wherein the shell further includes a folded portion extending orthogonally away from the rib into a portion of the support.

In an alternative embodiment, the shell is made from carbon fiber, which can include either long or short fibers. Further, the shell may include a layer of polymer overmolded on the carbon fiber.

A further embodiment of the present invention relates to a femoral component for use in connection with a joint replacement for a patient. The femoral component includes a support and a shell affixed to the support. The shell is shaped so as to provide an articulation surface for the joint and the support is structured to mate with a prepared surface of the joint and to space apart the shell at a predetermined distance therefrom.

In a preferred embodiment, the prepared joint is the knee, and the articulation surface is formed so as to replicate the anatomy of an articulation surface of a femoral condyle. In such an embodiment, the support bone engaging surface is structured to mate with a prepared surface of the distal femur.

In an alternative embodiment, the prepared joint is the hip and the articulation surface is formed so as to replicate the anatomy an articulation surface of a femoral head. In such an embodiment, the support surface forms a stem being adapted to mate with the inside surface of a prepared femoral canal.

BRIEF DESCRIPTION OF THE DRAWINGS

The present invention will be better understood on reading the following detailed description of nonlimiting embodiments thereof, and on examining the accompanying drawings, in which:

FIG. 9 is a cross section view taken along line 9-9 in FIG. 5;

FIG. 10 is a hip implant according to an alternative embodiment of the present invention; and FIG. 11 is a cross section view taken along line 11-11 in FIG. 10.

DETAILED DESCRIPTION

Figure 1:
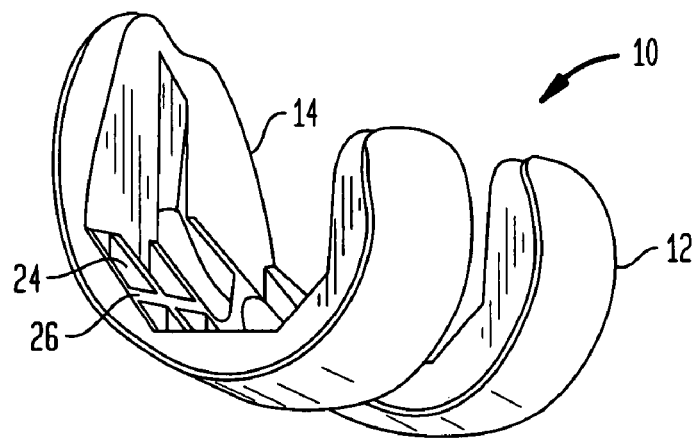
FIG. 1 is an isometric view of the trial implant according to an embodiment of the present invention.

In describing the preferred embodiments of the subject matter illustrated and to be described with respect to the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

Referring to the drawings, wherein like reference numerals represent like elements, there is shown in FIGS. 1-6, in accordance with a preferred embodiment of the present invention, more particularly, a femoral implant 10 used during a TKR procedure. The particular implant shown is preferably used as a trial implant; however it may be used as any type of femoral implant. Generally, the implant of the present invention has two primary surfaces thereof, including an articulating surface 12, and a bone engaging surface 14. Preferably, articulating surface 12 is shaped so as to approximately replicate the shape of the distal femur and, in particular, the articulating surfaces of the femoral condyles. It is not necessary that articulating surface 12 match the particular anatomy of the knee of the particular patient. Further, articulating surface is preferably designed to engage an artificial tibial implant (not shown). The desired general shape and design for articulating surfaces of femoral implants is known in the art.

Bone engaging surface 14 is formed to match the surface of the distal femur once the bone has been resected. Resection of the distal femur may vary by application, but is generally performed so as to remove one or both of the femoral condyles. This is generally done by making a series of cuts in the distal femur, the positioning and formation of which is known in the art. The femoral implant bone engaging surface shown in FIGS. 1-6 has a profile that matches one known shape for the resected distal femur; however, other shapes may be now known or later contemplated and corresponding shapes for bone engaging surface 14 would be understood by one having reasonable skill in the art.

The geometry of both articulating surface 12 and bone engaging surface 14 lead to bone engaging surface 14 being spaced proximally of articulating surface 12 and being spaced apart at a distance therebetween. Accordingly, implant 10 has a thickness that is appropriate to provide the preferred spacing between articulating surface 12 and bone engaging surface 14. Preferably, the general shape of implant 10 is similar to that of implants known in the art. In particular, when implant 10 is to be used as a femoral trial, it is preferred that implant 10 matches the shape of a corresponding permanent implant as closely as possible.

Figure 2:
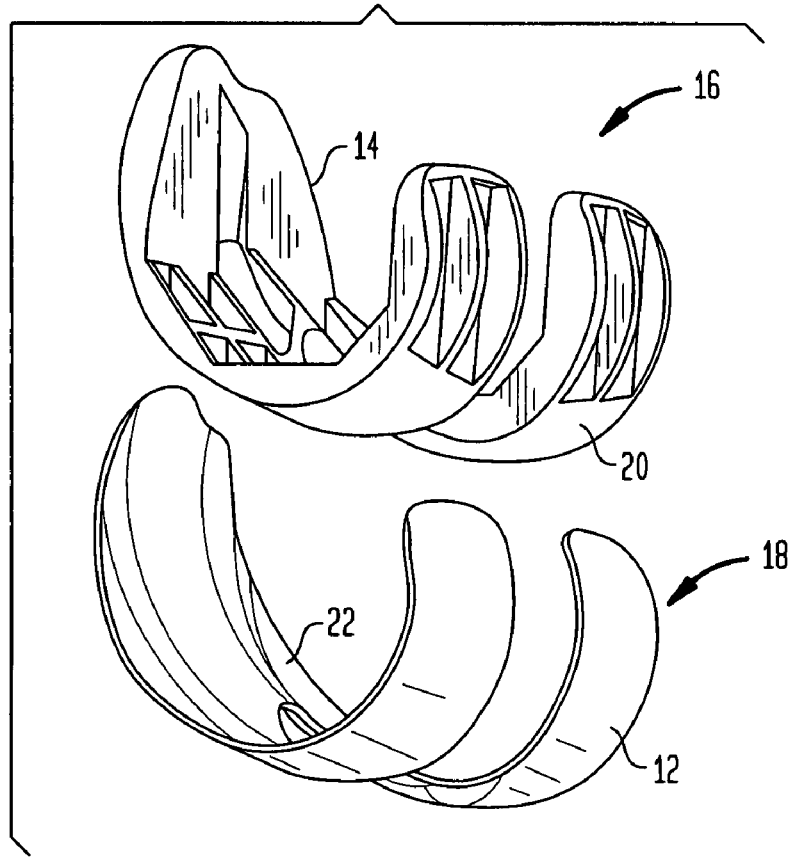
FIG. 2 is an assembly view of the trial implant according to an embodiment of the present invention.
Figure 3:
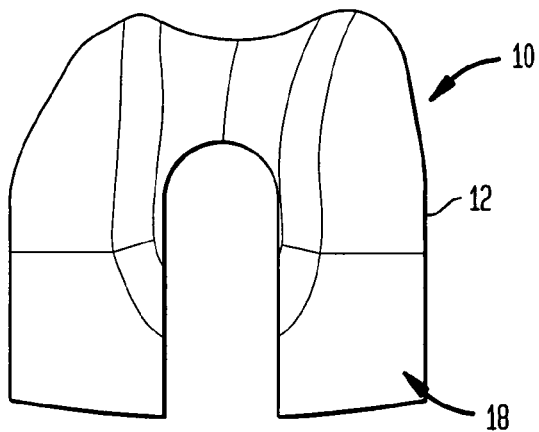
FIG. 3 is a distal to proximal view of an implant according to an embodiment of the present invention.
Figure 4:
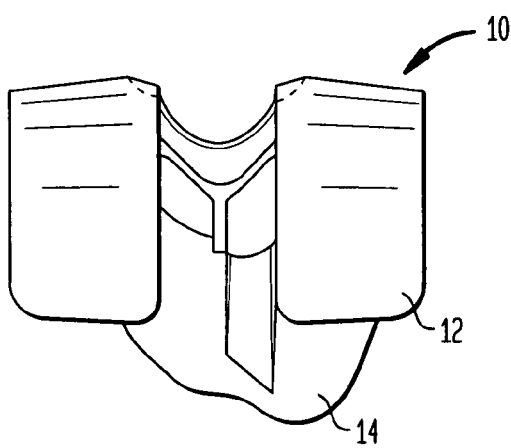
FIG. 4 is a posterior to anterior view of an implant according to an embodiment of the present invention.
Figure 6:
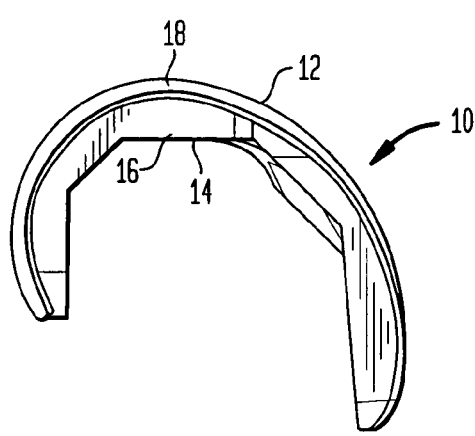
FIG. 6 is a lateral view of an implant according to an embodiment of the present invention.
Figure 5:
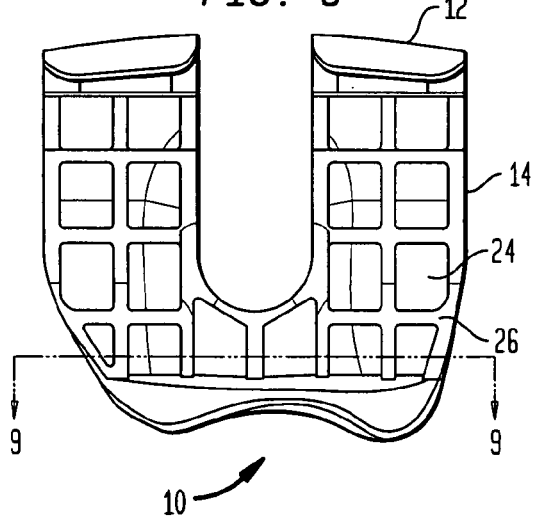
FIG. 5 is a proximal to distal view of an implant according to an embodiment of the present invention.

As best shown in FIG. 2, implant 10 is preferably formed from two separate parts. Support 16 is interposed within shell 18 and forms bone engaging surface 14 therein. The outside surface 20 of support 16 is designed to substantially mate with inside surface 22 of shell 18. Shell 18 forms articulating surface 12, and preferably has a thin, substantially uniform thickness such that the shape of inside surface 22 substantially matches that of articulating surface 12. Accordingly, support 16 provides a majority of the appropriate spacing between articulating surface 12 and bone engaging surface 14.

Various materials can be used in formation of shell 18 and support 16. Acceptable materials for shell 18 include various metals, such as CoCr, SS and aluminum alloys, or polymeric material, such as polyetheretherketone (PEEK). If a polymeric material is used to form shell 18, the polymer may be reinforced with carbon fiber, including long short or micro fibers, as they are known in the art. Preferably, shell is formed from a metal, such as CoCr or SS having a thickness between about 0.015 inches and about 0.065 inches, or aluminum alloy having a thickness between about 0.030 inches and about 0.080 inches. In a preferred embodiment, shell 18 is formed from SS and has a thickness of about 0.040 inches.

Various materials may also be used in the formation of support 16. Acceptable materials for support 16, include metal and polymeric material. Metals may include CoCr, aluminum alloys and SS, and polymeric materials may include ULTEX®, PEEK, polycarbonate, polysulphone, XYLAR®, and LEXAN®. In an embodiment of the present invention, support 16 can be made from a fiber-reinforced polymeric material. Such materials may include PEEK reinforced with carbon fibers, which may comprise long, short or micro fibers. Further, support 16 is preferably formed with a series of recesses 24 therein. The inclusion of recesses 24 within support 16 reduces the amount of material used to form support 16, which may reduce the overall cost of implant 10 and/or the weight thereof. Further, the formation of recesses 24 in support 16 results in the formation of a number of ribs 26 within the structure of support 16. Ribs may increase the overall strength of support 16 and, thus, of implant 10, allowing for less-rigid and, possibly, less expensive materials to be used. Still further, the inclusion of recesses 24 allows the material from which support 16 is formed to have a more uniform thickness. This is advantageous when forming support 16 using an injection molding process because uniform material thickness allows the material throughout the entire part to cool (and thus, shrink) uniformly. This helps prevent the part from warping during cooling.

In a preferred embodiment of implant 10, shell 18 is formed from a metal, preferably CoCr or SS and support 16 is formed from a polymeric material, preferably XYLAR®. In such an arrangement, shell 18 is more preferably formed using a hydroform process. Hydroform is a process that is generally known in the art and is useful for imparting complex, three-dimensional ("3D") shapes into metal. Preferably, shell 18 is formed using a vertical hydraulic hydroforming press. Such a process can be carried out by Aero Trades Manufacturing, located at 65 Jericho Turnpike, Mineola, N.Y. It is preferred that a metal subjected to a hydroform process is thin enough to be accurately formed by the process. It is also preferred that the material be thick enough to retain the shape imparted therein. The ideal thickness for shell in this embodiment will vary by the material and specific geometry used and will be known by those having reasonable skill in the art. The use of a hydroform process to form shell 18 reduces the need for the additional process steps of CNC grinding or polishing, as are needed with a casting process.

Generally, the combination of a shell 18 made from hydroformed metal and a support 16 made from a polymeric material allows for an implant 10 which is appropriately shaped and sufficiently rigid to provide acceptable trial joint reduction, while being lightweight and cost-effective from a manufacturing standpoint. The lightweight design of such an implant 10 allows for easy transportation of a number of such implants 10 when used in a set of trial implants. Further, the cost-effective manufacture of such implants makes it reasonable to use each of such implants in only one surgical procedure. The provision of such disposable trial implants may eliminate the need to design such an implant to withstand multiple autoclave cycles, and to withstand multiple trial reductions, further lowering the manufacturing cost thereof.

Shell 18 may be affixed to support 16 by a variety of methods, including using adhesives. Additionally, fixation elements such as screws, bolts or rivets may be included within implant 10 to secure shell 18 to support 16. Further, corresponding tabs may be formed in appropriate portions of shell 18 and support 16 to achieve fixation therebetween.

Figure 7:
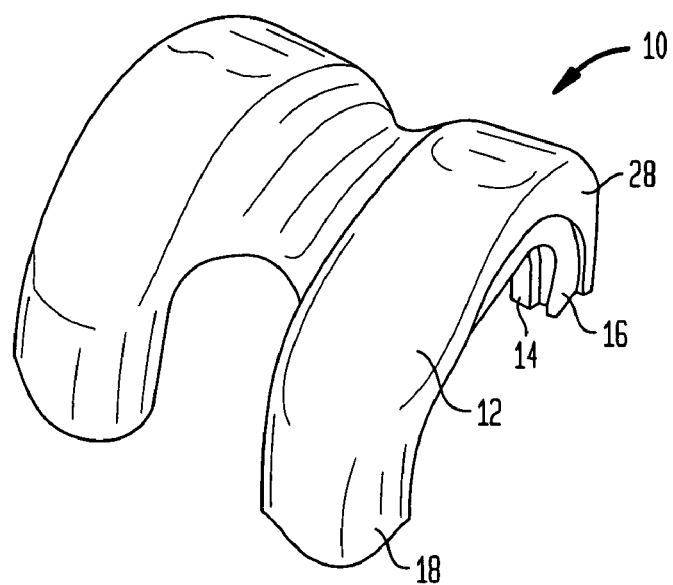
FIG. 7 is an isometric view of the outer surface of an implant according to a further embodiment of the present invention.
Figure 8:
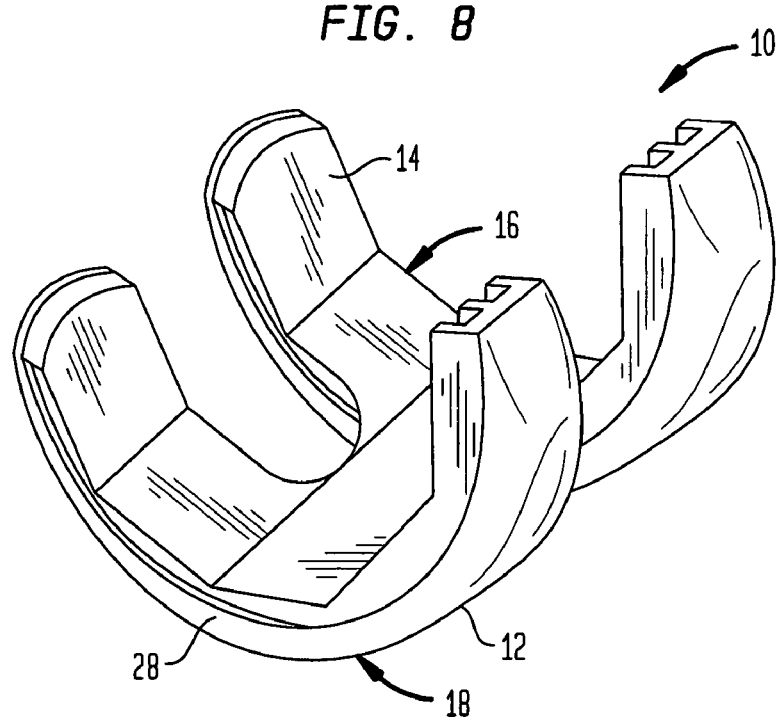
FIG. 8 is an isometric view of a bone engaging surface of an implant according to a further embodiment of the present invention.

Referring now to FIGS. 7-8, a further embodiment of the present invention is shown wherein implant 10 is formed from support 16 and shell 18 in a manner similar to that of implant 10 described with reference to FIGS. 1-6. Implant 10 of the present embodiment includes shell 18 having a generally proximally extending rib or flange 28 extending along at least a portion of the outer periphery of shell 18 and preferably the entire outer periphery. The integral formation of rib 28 within the outer periphery of shell 18 increases the rigidity of shell 16, and accordingly of implant 10 overall. Rib 28 may be formed in a metal shell 16 by hydroforming.

More preferably, as shown in FIG. 9, shell 18 further includes folded section 30 extending inwardly from the upper surface of rib 28. Folded section 30 further increases the rigidity of shell 18 and implant 10, especially with respect to flexion of implant 10 in the anterior-posterior direction. Additionally, folded section 30 provides for a means of affixation between support 16 and shell 18. In particular, in a preferred embodiment of the present invention, shell 18 is formed from hydroformed metal, preferably CoCr or SS, and support 16 is formed from a polymeric material. In this embodiment, support 16 is formed by insert molding the polymeric material onto shell 18. In such a process, support 16 is formed by injection-molding of a polymeric material into an appropriately shaped mold into which a pre-formed shell 18 has been inserted. Because the molten polymeric material can easily flow into and around any geometry formed in the shell, including rib 28 and folded portion 30, direct contact between the polymeric support 16 and the shell 18 may be the primary method of attachment therebetween. Incorporation of rib 28 and folded portion 30 furthers this attachment because the polymer flows into the shell, fully encasing the folded portion 30. This direct contact between the two materials along the periphery of the shell provides sufficient purchase to fully affix the shell 18 to the support 16.

Additionally, as shown in FIG. 9, shell 16 may have post 32 affixed to inside surface 22 thereof. Preferably, post 32 is either T-shaped, as shown, or includes a "stepped" geometry, as it is known in the art. Inclusion of this form of post 32 provides additional contact points between shell 18 and support 16. Post 32 may be fabricated to provide geometry similar to folded portion 32 discussed above, wherein the contact between post 32 and the hardened polymer comprising support 16 creates additional purchase, further affixing shell 18 to support 16. Post 32 may be added to inside surface 22 after formation of shell 18 and affixed thereto using welding or a similar process. In this particular embodiment, implant 10 may include a plurality of posts 32.

In an alternative embodiment of the present invention, an implant 10 generally similar in structure to those discussed with respect to FIGS. 1-9 is made from polymeric reinforced carbon fiber. Carbon fiber is a reinforcing fiber known for its lightweight, high strength and high stiffness. Carbon fiber is produced by a high-temperature stretching process of an organic precursor fiber based on polyacrylonitrile ("PAN"), rayon, or pitch in an inert atmosphere at temperatures above 1,800 degrees, Fahrenheit. Fibers can be transformed by removing more non-carbon atoms via heat treating above 3,000 degrees Fahrenheit. After these fibers are produced, they can be utilized in many different forms. They can be woven into long, dry fabric, pre-impregnated with resin, wound onto spools for use in filament winding, or braided and chopped into small fibers. There are several ways in which to produce components using carbon fiber; however, all of such processes require the use of a mold to impart the necessary geometry into the carbon fiber. The mold used in such a process defines the shape of the component. Accordingly, any component that can be molded can be formed from carbon fiber. For example, femoral trials can be created using carbon fibers. In a preferred embodiment, the femoral trial can be molded using a two-part mold; one mold to define the bone engaging surface 14 and the other to form the articulating surface 12.

Molding processes used to form a trial from carbon fiber include autoclave molding, compression molding, bladder molding, resin transfer molding ("RTM") roll wrapping, filament winding, and wet lay-up. Any of these methods can be used to produce knee femoral trials for TKR and hip stem trials for THR. All of these types of molding processes force the carbon and resin to conform to the desired shape using heat and/or pressure. Once the part has cured, it maintains its shape permanently and the composite construction provides sufficient rigidity to allow the implant 10 to perform equivalently to a metal trail during trial reduction. The use of micro carbon fibers reduces manufacturing costs, but also reduces material strength. Preferably, implant 10 of the present embodiment is molded from a polymer reinforced with long fiber, which is then overmolded with a "neat" polymer.

While robust, the composite construction of the implant 10 of the present embodiment of the invention possesses less resistance to the effects of repeated autoclave cycling than cast CoCr or SS trials. Previously known trials have been designed to survive multiple autoclave cycles and retain the rigidity they had before the first use thereof. Implant 10 of the present embodiment need only possess sufficient rigidity for a single use and needs not have the same robustness of reusable trials. Implant 10 of the current embodiment, however, has a weight that is significantly less than reusable trials, and thus alleviates many of the problems associated with the weight thereof.

Implant 10 of the present embodiment can be formed using a two-part structure as shown in FIGS. 1-9, wherein shell 18 includes articulating surface 12, and support 16 includes bone engaging surface 14 and appropriately spaces apart articulating surface 12 from bone engaging surface 14. In such an embodiment, shell 18 is preferably affixed to support 16 using an adhesive or an epoxy compound. Alternatively, implant 10 can be molded in a unitary form, having articulating surface 12 and bone engaging surface 14 formed therein.

Referring now to FIG. 10, an alternative embodiment of the present invention is shown in which implant 110 is in the form of a hip stem trial as is used in a THR procedure. The use of hip stem trials is similar to that of femoral trials. Generally, implant 10 replicates the shape and joint kinematics of a permanent implant and is used in trial reduction of the replacement joint. Implant 110 of the present invention includes a modular articulating surface 112, which replicates a resected femoral head and is generally in the shape of a portion of a sphere. Further, implant 110 includes a bone engaging stem portion having surface 114, which is appropriately shaped so as to fit within a resected proximal femoral canal. Support 116 gives shape to bone engaging surface 114 and appropriately spaces apart articulating surface 112 therefrom. Implant 110 can be fabricated using a hydroform process as discussed above by forming two half-shells with the hydroform process and then assembling the half-shells onto a plastic inner structure. Alternatively, implant 110 can be formed using a tube hydroforming process, which can be carried out by Vari-Form, which is located at, 250 Lothian Ave., Strathory, Ontario, Calif.

Support 116 can be formed from various materials including metal. In one form of the present embodiment, support 116 is made from a metal tube, which is subjected to pressure to impart the appropriate shape therefor. In an alternative embodiment, support 116 is made from a molded polymeric material, which may be fiber reinforced in a manner similar to other embodiments of the present invention discussed above. The general shape of the femoral head may be provided within support 116. In such an arrangement, shell 118 may be affixed thereto to provide implant 110 with articulating surface 112. Shell 118 can be formed from various metals including CoCr and SS or molded polymeric material, which may be fiber reinforced. A metal shell 118 may be formed by hydroforming, as discussed above. Alternatively, articulating surface 112 may be provided on support 116 in a unitary fashion.

Although the various embodiments of the present invention have been discussed as they apply either to the human knee and hip joints, one having reasonable skill in the art upon reading this disclosure would understand that the present invention can be used to form other joints of human or animal bodies. Such joints may include the elbow, wrist, shoulder, etc.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A femoral component for use in connection with knee anthroplasty, comprising:
   a. a support having a contoured inner bone engaging surface and a curved outer surface, the inner bone engaging surface having a profile matching a prepared distal femur; and
   b. a shell having a thickness between 0.015 to 0.065 inches affixed to said support outer surface, the shell having a uniform thickness; said shell having an outer surface forming a medial and a lateral condyle to provide a curved articulation surface for engaging a tibia that substantially replicates the shape of a medial and lateral femoral condyle and an inner surface for receiving an outer surface of said support, the inner surface of the shell having a curved surface matching the outer curved articulation surface of the shell, the curved outer surface of the support matching the shape of the shell inner surface; and wherein said support bone engaging surface is structured to mate with a prepared surface of the distal femur and said support spaces said shell outer surface at a predetermined distance from said prepared surface, the support inner surface formed at least in part by a multiplicity of spaced ribs forming a plurality of recesses therebetween, the ribs extending through the support from the bone engaging surface to the curved outer surface and contacting the medial and lateral condyles of the shell, the support curved outer surface fixedly attached to the inner surface of the shell, the ribs having end surfaces for contacting bone, the support providing a majority of the spacing between the articulation surface and the bone engaging surface.

2. The femoral component of claim 1, wherein said support is formed from a plastic.

3. The femoral component of claim 1, wherein said shell is made from a metal.

4. The femoral component of claim 3, wherein said metal is stainless steel.

5. The femoral component of claim 3, wherein said metal is Cobalt Chrome.

6. The femoral component of claim 3, wherein said shell is formed using a hydroform process.

7. The femoral component of claim 3, wherein said shell has an edge portion which is further shaped so as to provide an outer profile having a rib extending therefrom in a direction away from said articulation surface.

8. The femoral component of claim 7, wherein said support is made from a polymeric material and wherein said shell further includes a folded portion extending orthogonally from said rib into a portion of said support.

9. The femoral component of claim 1, wherein said shell is made from carbon fiber composite.

10. The femoral component of claim 9, wherein said carbon fiber composite comprises long carbon fibers.

11. The femoral component of claim 9, wherein said carbon fiber composite comprises short carbon fibers.

12. The femoral component of claim 11, wherein said shell further includes a layer of polymer overmolded on said carbon fiber composite.

13. The femoral component of claim 9, wherein said shell is formed using an inner mold and an outer mold, said outer mold forming the shape of the articulating surface and said inner mold forming said inner surface to mate with said support.

14. A femoral component for use in connection with a joint replacement for a patient, comprising:
   a. a support having an inner bone engaging surface and a curved outer surface, the inner bone engaging surface having a profile matching a prepared distal femur; and
   b. a shell having a thickness between 0.015 and 0.065 inches and having a curved outer articulation surface forming medial and lateral condylar portions and an inner surface affixed to said support outer surface, the shell having a uniform thickness defined by the inner and outer surfaces so that a shape of the inner shell surface matches the curved shape of the shell outer articulation surface, the curved outer surface of the support matches the curved shape of the shell inner surface; and
   wherein said shell outer surface is shaped so as to provide an articulation surface for the joint; and wherein said support is structured to mate with a prepared surface of the distal femur and to space apart said shell at a predetermined distance therefrom, the support inner surface formed at least in part by a multiplicity of spaced ribs forming a plurality of recesses therebetween, the ribs extending through the support from the inner bone engaging surface to the curved outer surface and contacting the inner surface of each of the medial and lateral condylar portions of the shell, the support outer surface fixedly attached to the inner surface of the shell, the ribs having first end surfaces for contacting bone and a second end surfaces fixed to the shell inner surface, the support providing a majority of the spacing between the articulation surface and the bone engaging surface.

15. The femoral component of claim 14, wherein the prepared surface of the joint is the knee, and wherein said articulation surface is formed so as to replicate the anatomy of an articulation surface of a femoral condyle.

16. The femoral component of claim 15, wherein said inner bone engaging surface is structured to mate with a prepared surface of the distal femur.

17. The femoral component of claim 14, wherein said shell and said support are made from molded carbon fiber.

18. The femoral component of claim 14, wherein said shell and said support are made from a metal.

* * * * *